United States Patent
Maxwell

(10) Patent No.: US 6,787,685 B2
(45) Date of Patent: Sep. 7, 2004

(54) INBRED CARROT LINE S-D813B

(75) Inventor: Robert V. Maxwell, Payette, ID (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 10/338,766

(22) Filed: Jan. 7, 2003

(65) Prior Publication Data

US 2003/0154519 A1 Aug. 14, 2003

Related U.S. Application Data

(60) Provisional application No. 60/356,369, filed on Feb. 12, 2002.
(51) Int. Cl.⁷ .............................. A01H 1/00; A01H 4/00; A01H 5/00; C12N 15/82
(52) U.S. Cl. ....................... 800/298; 435/410; 800/260; 800/266; 800/278; 800/279; 800/280; 800/300; 800/301; 800/302
(58) Field of Search ................................ 800/278, 260, 800/298, 266; 435/468, 419, 410

(56) References Cited

PUBLICATIONS

Quattrocchio et al 1998, The Plant Journal 13(4): 475–488.*

Goldman 1996, HortScience 31(5): 882–883.*

\* cited by examiner

*Primary Examiner*—Amy J. Nelson
*Assistant Examiner*—David H Kruse
(74) *Attorney, Agent, or Firm*—Jondle & Associates P.C.

(57) ABSTRACT

An inbred carrot line, designated S-D813B, is disclosed. The invention relates to the seeds of inbred carrot line S-D813B, to the plants of inbred carrot line S-D813B and to methods for producing a carrot plant, either inbred or hybrid, by crossing the inbred line S-D813B with itself or another carrot line. The invention further relates to methods for producing a carrot plant containing in its genetic material one or more transgenes and to the transgenic plants produced by that method and to methods for producing other inbred carrot lines derived from the inbred S-D813B.

20 Claims, No Drawings

INBRED CARROT LINE S-D813B

CROSS REFERENCE

This application claims benefit of U. S. Provisional Application No. 60/356,369, filed Feb. 12, 2002.

BACKGROUND OF THE INVENTION

The present invention relates to a new and distinctive carrot inbred line, designated S-D813B. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, vegetable and agronomic quality such as uniform taper, color, content in soluble solids, low bitterness, high moisture, resistance to diseases and insects, and tolerance to drought and extreme temperatures. With mechanical harvesting of carrots for process purpose, i.e. juice, fresh market, packaged "baby carrots", cello-pak, etc, uniformity of plant characteristics such as germination, growth rate, maturity and plant uniformity is also important.

Practically speaking, all cultivated and commercial forms of carrot belong to a species referred to as *Daucus Carota*. *Daucus Carota* is a complex species, botanically comprising both wild and cultivated carrots. Carrots belong to the family Apiaceae which is characterized as having dissected leaves, umbellate inflorescences and fruits that are schizocarps (which split into two mericarps). Several hundred varieties of carrot exist in the market today.

Carrots originated in South Asia, in what is now Afghanistan, Iran and Pakistan. By 900 to 1000 A.D. they were being grown from India to the Eastern Mediterranean. By the 1300's purple and yellow carrots had spread as far as Western Europe and China. The first appearance of white and orange carrots in Europe was during the 1700's. Orange carrots soon displaced other colors and today predominate throughout the world. Carrots are an excellent source of beta-carotene (pro-vitamin A) and the high pigment varieties are also an excellent source of antioxidants thought to help prevent cancer.

There are two main types of cultivated carrots. Eastern/Asiatic carrots are often called anthocyanin carrots because of their purple roots, athough some have yellow roots. They have pubescent leaves giving them a gray-green color and bolt easily. They have slightly dissected leaves with branched roots and are an annual plant. Western or carotene carrots have orange, red or white roots. These carrots were most likely derived from the first group by selection among hybrid progenies of yellow Eastern carrots, white carrots and wild subspecies grown in the Mediterranean. The leaves are strongly dissected, the roots are unbranched and they have bright green, sparsely hairy foliage and are biennial.

The biennial carrot is is a plant that only flowers every two years. In the first year the plant produces the edible root and a leafy top. If a carrot plant is left in the ground for another year, aided by a resting and cold vernalization period, it flowers and seeds are produced. Sexual reproduction in carrots is therefore not different from other flowering plants. Pollen is produced and transferred to the female part of the flower, the stigma. The pollen grain then delivers the sperm cells within it to the ovary via a long tube where fertilization takes place. The seeds are tiny—a teaspoon can hold almost 2000 seeds.

The carrot is a cool climate crop and can be sown early in the Spring in temperate climates or in the Fall or Winter in sub-tropical areas.

The Western carrot is by far the most popular carrot and is sub-divided into three groups: 1) Short-rooted varieties that mature more quickly and the first to be sown such as Amsterdam Forcing, Tiana, Early French Frame, Early Nantes, Champion Scarlet Horn. 2) Medium-rooted varieties are the most common type of commercially grown carrots. Varieties include Mokum, Flakkee, Autumn King, Chatenay Red Cored, Royal Chatenay. 3) Long-rooted varieties are usually grown in well-prepared and deep soils and include varieties New Red Intermediate and Saint Valery.

Carrots are widely used as a fresh market or processed product. As a crop, carrots are grown commercially wherever environmental conditions permit the production of an economically viable yield. Carrots are highly regarded for their nutritional value and their storability. In many parts of the world, carrots may provide a durable source of nutrition while maintained in very crude facilities. They are credited as a major source of pro-Vitamin A in the human diet. Carrots are widely adapted to various climates and growing conditions. A loose, well-drained soil for decent root growth and development is the main requirement for adequate production.

Fresh market carrots are available in the United States year round. Process carrots are used in many forms, as frozen pack in mixed or solo vegetables, canned as diced, sliced, or sticks, or as a major or minor part of many fruit juice drinks.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior carrot inbred lines and hybrids. The breeder initially selects and crosses two or more parental lines, followed by repeated selfing, sib-mating, and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same carrot traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new carrot inbred line.

The development of commercial carrot hybrids requires the development of homozygous inbred lines, the crossing of these lines, and the evaluation of the crosses. Pedigree, backcross or recurrent selection breeding methods are used to develop inbred lines from breeding populations. Breeding programs combine desirable traits from two or more inbred lines or various broad-based sources into breeding pools from which inbred lines are developed by selfing, sib-mating, and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars or new parents for hybrids.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., "Principles of Plant Breeding" John Wiley and Son, pp. 115–161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny.

Carrots are an important and valuable field crop. Thus, a continuing goal of plant breeders is to develop stable, high yielding carrot hybrids that are agronomically sound. The reasons for this goal are obviously to maximize the amount of fruit produced on the land used as well as to improve the fruit qualities. To accomplish this goal, the carrot breeder must select and develop carrot plants that have the traits that result in superior parental lines for producing hybrids.

SUMMARY OF THE INVENTION

According to the invention, there is provided a novel inbred carrot line, designated S-D813B. This invention thus relates to the seeds of inbred carrot line S-D813B, to the plants of inbred carrot line S-D813B and to methods for producing a carrot plant produced by crossing the inbred line S-D813B with itself or another carrot line, and to methods for producing a carrot plant containing in its genetic material one or more transgenes and to the transgenic carrot plants produced by that method. This invention also relates to methods for producing other inbred carrot lines derived from inbred carrot line S-D813B and to the inbred carrot lines derived by the use of those methods. This invention further relates to hybrid carrot seeds and plants produced by crossing the inbred line S-D813B with another carrot line.

The carrot plant of the invention may further comprise, or have, a cytoplasmic factor or other factor that is capable of conferring male sterility. Male sterility may also be provided by nuclear genes such as the recessive ms gene. Parts of the carrot plant of the present invention are also provided, such as e.g., pollen obtained from an inbred plant and an ovule of the inbred plant.

In another aspect, the present invention provides regenerable cells for use in tissue culture of inbred carrot plant S-D813B. The tissue culture will preferably be capable of regenerating plants having the physiological and morphological characteristics of the foregoing inbred carrot plant, and of regenerating plants having substantially the same genotype as the foregoing inbred carrot plant. Preferably, the regenerable cells in such tissue cultures will be embryos, protoplasts, meristematic cells, callus, pollen, leaves, anthers, stems, petioles, roots, root tips, fruits, seeds, flowers, cotyledons, hypocotyls or the like. Still further, the present invention provides carrot plants regenerated from the tissue cultures of the invention.

Another objective of the invention is to provide methods for producing other inbred carrot plants derived from inbred carrot line S-D813B. Inbred carrot lines derived by the use of those methods are also part of the invention.

The invention also relates to methods for producing a carrot plant containing in its genetic material one or more transgenes and to the transgenic carrot plant produced by that method.

In another aspect, the present invention provides for single gene converted plants of S-D813B. The single transferred gene may preferably be a dominant or recessive allele. Preferably, the single transferred gene will confer such trait as male sterility, herbicide resistance, insect resistance, resistance for bacterial, fungal, or viral disease, male fertility, improved harvest characteristics, enhanced nutritional quality, improved processing characteristics. The single gene may be a naturally occurring carrot gene or a transgene introduced through genetic engineering techniques.

The invention further provides methods for developing carrot plant in a carrot plant breeding program using plant breeding technique including recurrent selection, backcrossing, pedigree breeding, restriction fragment length polymorphism enhanced selection, genetic marker enhanced selection and transformation. Seeds, carrot plant, and parties thereof produced by such breeding methods are also part of the invention.

DEFINITIONS

In the description and tables that follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Spring Stand. Spring stand is a visual rating (0–10 points) where the carrots are planted thick and thinned to approximately 6 inch spacing in the Spring. Prior to thinning, a subjective notation is made regarding appearance and mortality through the Winter.

Plant Vigor: The plant vigor is a visual rating (0–10 points, 10 is most vigorous) that is very subjective. To rate vigor, the best vigor and the poorest vigor within a trial is determined and then the plant vigor scoring scale is based on these examples.

Umbel Area: The umbel area is a subjective measure (0–10 points, 10-largest umbel area) that takes into consideration the umbel size and number of umbels.

Quantitative Trait Loci (QTL) Quantitative trait loci refer to genetic loci that control to some degree numerically representable traits that are usually continuously distributed.

Lodging and Disease Tolerance. The lodging and disease tolerance is a visual rating (0–10 points, 10=most tolerant) and is based on any occurrence of lodging or potential disease problems, such as bacterial rot, powdery mildew, etc., are noted.

Relative Seed Yield. Relative seed yield is a score (0–30 points) that is given when the seed is mature, five plants are harvested from each plot. The umbels are dried, threshed and the seed cleaned and weighed. The yields are adjusted to set 30 points for the highest yielding lines with lower yields based on a percentage of the highest.

Relative maturity: relative maturity is an indication of time until a carrot is ready for harvest. Various inbreds respond at different rates to bloom development and receptivity. Further differentiation is noted through rate of plant senescence and seed ripening. New inbreds are compared to known commercial inbreds to establish a point of reference.

Bee Activity. Bee activity is a score (0–20 points) that is done twice a week beginning with the initial bloom of the early lines and ending with final bloom of the late lines. Readings are taken around noon. Counts are of total bees visible per 20-foot replicate by standing at one end and slowly sweeping the line of vision from one end to the other. Five observations per rep are taken beginning with initial bloom and ending two weeks later. This carries the readings past peak bloom and heading towards decline.

Seed Index: Seed index is a comparative value of seed yield of any individual inbred to a control inbred. Each year, the control inbred value is adjusted to a set point of 100 and all comparative inbreds adjusted to the same ratio accordingly. This is an attempt to compensate for the year-to-year fluctuations for seed yield, which occur naturally.

Nick or Nicking A term used to describe the timing of bloom between two or more different inbreds. A good nick means that two desired inbreds bloom at the same time.

Bloom period: The amount of time that an umbel, in it's entirety, is receptive for pollination. This begins at initial bloom, carries through peak bloom and ends at bloom decline.

King umbels: The primary umbel which develops from the main seed stalk.

Secondary umbels: The group of umbels which develop from second order side branch stalks off of the main stalk Tertiary umbels. The group of umbels which develop from third order side branch stalks off of second order stalks.

DETAILED DESCRIPTION OF THE INVENTION

Inbred carrot line S-D813B is a carrot with superior characteristics, and provides an excellent parental line in crosses for producing first generation ($F_1$) hybrid carrots. Inbred carrot line S-D813B is best adapted to deep sandy loam soils such as those found in the cut and peel growing regions of Southern California. The line can be used to produce hybrids having a maturity from 110 to 150 days from seedling to harvest maturity. Inbred carrot line S-D813B provides an unique cylindrical shape of a slender 1 to 2 cm. diameter root with uniform fill from crown to tip. This length can range from 25 to 40 cm, depending upon the hybrid combination. This shape is highly beneficial for the production of numerous uniform segments of the size grade desired in the cut and peel 'baby carrot' industry.

During the development of S-D813B, the pedigree selection method was used for inbred advancement. Sib-mating of selected pairs resulted in the development of a highly uniform, cylindrical phenotype. This population was used as a pollinator in hybrid combination with several male steriles of known high general combining ability.

S-D813B is similar to the carrot 364334301B with numerous differences. The present invention is more cylindrical and has a sweeter flavor than 364334301 B.

During the development of the line, crosses were made to inbred testers for the purpose of estimating the line's general and specific combining ability, and parallel evaluations were run in the U.S. and Canada. The inbred was evaluated further as a line and in numerous crosses and has proven to have a good combining ability in hybrid combinations.

The inbred line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in S-D813B.

Inbred carrot line S-D813B has the following morphologic and other characteristics (based primarily on data collected at Payette, Id.).

VARIETY DESCRIPTION INFORMATION

Table A

PLANT TYPE: Carrot
REGION WHERE DEVELOPED: Seed—Idaho, Root Selection—Imperial Valley, Calif.

AREA OF BEST ADAPTATION IN THE USA: Bakersfield, Cuyama Valley, and Imperial Valley, Calif.
MATURITY: 120–130 days
Size: (length, diameter, height) L=17 to 20 cm, D=1 to 1.5 cm
Color Moderate, uniform Orange
Leaf description Foliage height (Imperial Valley) 30 to 40 cm

Further Emdodiments of the Invention

This invention also is directed to methods for producing a carrot plant by crossing a first parent carrot plant with a second parent carrot plant wherein either the first or second parent carrot plant is an inbred carrot plant of the line S-D813B. Further, both first and second parent carrot plants can come from the inbred carrot line S-D813B. Still further, this invention also is directed to methods for producing an inbred carrot line S-D813B-derived carrot plant by crossing inbred carrot line S-D813B with a second carrot plant and growing the progeny seed, and repeating the crossing and growing steps with the inbred carrot line S-D813B-derived plant from 0 to 7 times. Thus, any such methods using the inbred carrot line S-D813B are part of this invention: selfing, backcrosses, hybrid production, crosses to populations, and the like. All plants produced using inbred carrot line S-D813B as a parent are within the scope of this invention, including plants derived from inbred carrot line S-D813B. Advantageously, the inbred carrot line is used in crosses with other, different, carrot inbreds to produce first generation ($F_1$) carrot hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which carrot plants can be regenerated, plant calli, plant clumps and plant cells that are intact in plants or parts of plants, such as embryos, pollen, ovules, flowers, leaves, stalks, and the like.

As it is well known in the art, tissue culture of carrot can be used for the in vitro regeneration of carrot plants. Tissues cultures of various tissues of carrot and regeneration of plants therefrom are well known and published. By way of example, a tissue culture comprising organs has been used to produce regenerated plants as described in Girish-Chandel et al., *Advances in Plant Sciences*. 2000, 13: 1, 11–17, Costa et al., *Plant Cell Report*. 2000, 19: 3 327–332, Plastira et al., *Acta Horticulturae*. 1997, 447, 231–234, Zagorska et al., *Plant Cell Report*. 1998, 17: 12 968–973, Asahura et al., *Breeding Science*. 1995, 45: 455–459, Chen et al., *Breeding Science*. 1994, 44: 3, 257–262, Patil et al., *Plant and Tissue and Organ Culture*. 1994, 36: 2, 255–258. It is clear from the literature that the state of the art is such that these methods of obtaining plants are, and were, "conventional" in the sense that they are routinely used and have a very high rate of success. Thus, another aspect of this invention is to provide cells which upon growth and differentiation produce carrot plants having the physiological and morphological characteristics of inbred carrot line S-D813B.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed carrot plants, using transformation methods as described below to incorporate transgenes into the genetic material of the carrot plant(s).

Expression Vectors for Carrot Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983) Eck et al., *Plant Cell Report*, 14:5 299–304 (1995). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990<Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., *Plant Mol Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Charng et al., *Plant Science Limerick.* 1994, 98: 2, 175–183, Hu Wei e al., *In vitro Cellular and Developmental Biology Plant* 37:1 12–18 (2001), Agharbaoui et al., *Plant Cell Report* 15:1/2 102–105 (1995).

Recently, in vivo methods for visualizing GUS activity that do not require destruction of plant tissue have been made available. Molecular Probes publication 2908, Imagene Green™, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in carrot. Optionally, the inducible promoter is operably linked to a nucleotide sequence encoding a signal sequence which is operably linked to a gene for expression in carrot. With an inducible promoter the rate of transcription increases in response to an inducing agent.

Any inducible promoter can be used in the instant invention. See Ward et al., *Plant Mol. Biol.* 22:361–366 (1993).

Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in carrot or the constitutive promoter is operably linked to a nucleotide sequence encoding a signal sequence which is operably linked to a gene for expression in carrot.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985), Tababeizadeh et al., *Plant Cell Report* 19:2 197–202 (1999), Kunik et al., *Acta Horticulturae* 447, 387–391 (1997) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO96/30530.

C. Tissue-specific or Tissue-preferred Promoters

A tissue-specific promoter is operably linked to a gene for expression in carrot. Optionally, the tissue-specific promoter is operably linked to a nucleotide sequence encoding a signal sequence which is operably linked to a gene for expression in carrot. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)), such as the promoter roID from *Agrobacterium rhizogenes* as mentioned in Grichko et al., *Plant Physiology and Biochemistry* 39:1 19–25 (2001); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is carrot. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the carrot Cf-9 gene for resistance to *Cladosporium fulvum*); Martin et al., *Science* 262:1432 (1993) (carrot Pto gene for resistance to *Pseudomonas syringae* pv. Carrot encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998. See also Mandaokat et al., *Crop Protection.* 2000, 19: 5, 307–312.

C. A lectin. See, for example, the disclose by Van Damme et al., *Plant Molec. Biol.* 24:25 (1994), who disclose the nucleotide sequences of several *Clivia miniata* mannose-binding lectin genes.

D. Genes coding for the coat proteins of the Cucumber Mosaic Comovirus (CMV), see Tomassoli et al., *Molecular Breeding.* 1999, 5: 2, 121–130, which once expressed in the plant allows it to be resistant to the CMV E. An enzyme inhibitor, for example, a protease or proteinase inhibitor or an amylase inhibitor or a polygalacturonase inhibitor protein. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor). Powell et al., *Molecular Plant Microbe Interaction.* 2000, 13:9 942–950 (carrotes transformed with pear fruit polygalacturonase inhibitor protein to inhibit the fungal pathogen endopolygalacturonase).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic peptide. See PCT application WO95/16776 (disclosure of peptide derivatives of Tachyplesin which inhibit fungal plant pathogens) and PCT application WO95/18855 (teaches synthetic antimicrobial peptides that confer disease resistance).

M. A membrane permease, a channel former or a channel blocker. For example, see the disclosure of Jaynes et al., *Plant Sci* 89:43 (1993), of heterologous expression of a cercropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1, 4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

S. A combination of Tobacco class I Chitinase and class I beta 1, 3, Glucanase gene that result in increased fungal resistance of the carrot expressing such genes. See Jongedijk et al., *Euphytica.* 1995, 85: 1/3,173–180.

2. Genes That Confer Resistance to a Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (*nitrilase* gene). Przibilla et al., *Plant Cell* 3:169 (1991), describe the transformation of Chiamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Increased flooding tolerance, for example by transforming a plant with a bacterial enzyme ACC deaminase. See Grichko et al., *Plant Physiology and Biochemistry.* 2001. 39: 1, 19–25

B. Improved juice and pulp viscosity, by transforming the plant with an antisense gene of polygalacturonase. For example, see Porretta et al., *Food Chemistry.* 1998, 62: 3, 283–290, or Errington et al., *Journal of the Science of Food and Agriculture,* 1998. 76: 4, 515–519.

C. Reduced polyethylene production in order to better control the ripening of the fruit, by transforming the plant with a S-adenosylmethionine hydrolase. See Good et al., *Plant Molecular Biology.* 1994, 26: 3, 781–790.

D. Obtained male sterile plants, especially useful in hybrid carrot production, by introduction of a gene encoding a tobacco PR Glucanase as described in WO9738116.

Methods for Carrot Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology,* Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology,* Glick B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Frary et al., *Plant Cell Report.* 1996, 16: 3/4, 235–240, Roehel et al., *Plant Cell Report.* 1993, 12: 11, 644–647, Hu-Wei et al., *In Vitro Cellular and Developmental Biology Plant.* 2001 37: 1, 12–18. *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 6,198,022 issued Mar. 6, 2001.

B. Direct Gene Transfer

Despite the fact the host range for Agrobacterium-mediated transformation is broad, some major cereal crop or vegetable species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992), Baum et al., *Plant Journal.* 1997, 12: 2, 463–469, Eck et al., *Plant Cell Report.* 1995, 14: 5, 299–304, Manzara et al., *Plant Molecular Biology Reporter* 12 :3 221–226 (1994).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.,* 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2–38, p 53 (1990); D'Halluin et al., *Plant Cell* 4:1495–1505 (1992) and Spencer et al., *Plant Mol. Biol.* 24:51–61 (1994) A transfer of chromosome has been reported from a transformed donor line of potato to a recipient line of carrot through microprotoplast PEG induced fusion. See Ramalu et al., *Theorical and Applied Genetics* 92: 3/4 316–325 (1996).

Following transformation of carrot target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular carrot line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred carrot plant is used in the context of the present invention, this also includes any single gene conversions of that inbred. The term single gene converted plant as used herein refers to those carrot plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental carrot plants for that inbred. The parental carrot plant which contributes the gene for the desired characteristic is termed the nonrecurrent or donor parent. This terminology refers to the fact that the nonrecurrent parent is used one time in the backcross protocol and therefore does not recur. The parental carrot plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a carrot plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility such as the PR glucanase gene, herbicide resistance such as pat or bar genes, resistance for bacterial, fungal (such as I genes used for resistance to fusarium oxysporum), or viral disease (such as genes TM1 and TM2 used for TMV resistance), insect resistance such as Cry1Ac or Mi genes, male fertility, enhanced nutritional quality, enhanced sugar content, enhanced processing qualities as shown in U.S. Pat. No. 6,072,106 by increasing the content in soluble solids, enhanced conservation and delayed ripening such as in using nor or rin genes, yield stability and yield enhancement. These genes are generally inherited through the nucleus. Some other known male sterility genes are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tables

In Table 1 that follows, the traits and characteristics of inbred carrot S-D813B are given in hybrid combination. The data collected are presented for key characteristics and traits.

In column 1 the pedigree is given. Columns 2, 3 and 4 give plant vigor, umbel area, lodging and disease ratings; columns 5, 6 and 7 list the spring stand, total bees and seed yield; and columns 8 and 9 list the seed index and rank.

TABLE 1

INBRED CARROT TRIALS
Payette, Idaho Research Station
3 Replications

| Pedigree | Plant Vigor (0–10) | Umbel Area (0–10) | Lodging Disease (0–10) | Spring Stand (0–10) | Total Bees (0–20) | Seed Yield (0–30) | Seed Index | Rank |
|---|---|---|---|---|---|---|---|---|
| CL1 | 9 | 8 | 7 | 7 | 13 | 16 | 114 | 5 |
| 364334301B | 6 | 8 | 7 | 6 | 11 | 13 | 97 | 21 |
| R75-17-B1B | 7 | 7 | 7 | 7 | 10 | 10 | 89 | 28 |
| S-D813B | 7 | 7 | 7 | 6 | 13 | 5 | 87 | 31 |

Deposit Information

A deposit of the Seminis Vegetable Seeds, Inc. proprietary inbred carrot line S-D813B disclosed above and recited in the appended claims has been made with the American Type Culture Collection (ATCC), 10801 University Boulevard, Manassas, Va. 20110. The date of deposit was May 7, 2004. The deposit of 2,500 seeds was taken from the same deposit maintained by Seminis Vegetable Seeds, Inc. since prior to the filing date of this application. All restrictions upon the deposit have been removed, and the deposit is intended to meet all of the requirements of 37 C.F.R. §1.801–1.809. The ATCC accession number is PTA-5949. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of an inbred carrot variety designated S-D813B, representative seed having been deposited under ATCC Accession No. PTA-5949.

2. A carrot plant, or parts thereof, produced by growing the seed of claim 1.

3. Pollen of the plant of claim 2.

4. An ovule of the plant of claim 2.

5. A tissue culture of regenerable cells from the plant of claim 2.

6. The tissue culture according to claim 5, wherein said tissue culture is produced from cells or protoplasts from a tissue selected from the group consisting of: leaves, pollen, embryos, cotyledon, hypocotyl meristematic cells, roots, root tips, anthers, flowers, seeds and stem.

7. A carrot plant regenerated from the tissue culture of claim 5, wherein the regenerated plant has all of the morphological and physiological characteristics of inbred carrot S-D813B, representative seed of said inbred carrot S-D813B having been deposited under ATCC Accession No. PTA-5949.

8. A method for producing a hybrid carrot seed comprising crossing a first parent carrot plant with a second parent carrot plant and harvesting the resultant hybrid carrot seed, wherein said first parent carrot plant or said second parent carrot plant is the carrot plant of claim 2.

9. A method for producing a transgenic carrot plant comprising transforming the carrot plant of claim 2 with a transgene wherein the transgene confers a characteristic selected from the group consisting of: herbicide resistance, insect resistance, resistance to bacterial disease, resistance to fungal disease, resistance to viral disease, and male sterility.

10. A transgenic carrot plant having the selected characteristic produced by the method of claim 9.

11. A method of producing a male sterile carrot plant comprising transforming the carrot plant of claim 2 with a transgene that confers male sterility.

12. A male sterile carrot plant produced by the method of claim 11.

13. A method of producing an herbicide resistant carrot plant comprising transforming the carrot plant of claim 2 with a transgene that confers herbicide resistance.

14. An herbicide resistant carrot plant produced by the method of claim 13.

15. A method of producing an insect resistant carrot plant comprising transforming the carrot plant of claim 2 with a transgene that confers insect resistance.

16. An insect resistant carrot plant produced by the method of claim 15.

17. A method of producing a disease resistant carrot plant comprising transforming the carrot plant of claim 2 with a transgene that confers disease resistance.

18. A disease resistant carrot plant produced by the method of claim 17.

19. A method of introducing a desired trait into carrot inbred line S-D813B comprising:

(a) crossing a S-D813B carrot plant representative seed having been deposited under ATCC Accession No. PTA-5949, with a plant of another carrot line that comprise a desired trait to produce F1 progeny plants, wherein the desired trait is selected from male sterility, herbicide resistance, insect resistance, bacterial resistance, fungal resistance or viral resistance;

(b) selecting F1 progeny plants that have the desired trait to produce selected F1 progeny plants;

(c) backcrossing the selected F1 progeny plants with a S-D813B plant to produce first backcross progeny plants;

(d) selecting backcross progeny plants that have the desired trait and physiological and morphological characteristics of carrot inbred line S-D813B to produce selected first backcross progeny plants; and (e) repeating steps (c) and (d) three or more times in succession to produce selected fourth or higher backcross progeny plants that comprise the desired trait and all of the physiological and morphological characteristics of carrot inbred line S-D813B as described in the Variety Description Information and as determined at a 5% significance level when grown in the same environmental conditions.

20. A carrot plant produced by the method of claim 19, wherein the plant has the desired trait and all of the physiological and morphological characteristics of carrot inbred line S-D813B as described in the Variety Description Information and as determined at a 5% significance level when grown in the same environmental conditions.

* * * * *